(12) United States Patent
Birkhoff et al.

(10) Patent No.: US 9,259,722 B2
(45) Date of Patent: Feb. 16, 2016

(54) PROCESS FOR PRODUCING CUMENE

(71) Applicant: BADGER LICENSING LLC, Boston, MA (US)

(72) Inventors: Ronald Birkhoff, Houston, TX (US); Shyh-Yuan H. Hwang, Needham, MA (US)

(73) Assignee: BADGER LICENSING LLC, Boston, MA (US)

( * ) Notice: Subject to any disclaimer, the term of this patent is extended or adjusted under 35 U.S.C. 154(b) by 0 days.

(21) Appl. No.: 14/415,960

(22) PCT Filed: Jul. 23, 2013

(86) PCT No.: PCT/US2013/051649
§ 371 (c)(1),
(2) Date: Jan. 20, 2015

(87) PCT Pub. No.: WO2014/018515
PCT Pub. Date: Jan. 30, 2014

(65) Prior Publication Data
US 2015/0182956 A1    Jul. 2, 2015

Related U.S. Application Data

(60) Provisional application No. 61/675,942, filed on Jul. 26, 2012.

(51) Int. Cl.
| | |
|---|---|
| C07C 407/00 | (2006.01) |
| B01J 29/90 | (2006.01) |
| C07C 2/86 | (2006.01) |
| B01J 29/08 | (2006.01) |
| B01J 29/40 | (2006.01) |
| B01J 29/70 | (2006.01) |
| B01J 38/04 | (2006.01) |
| B01J 38/10 | (2006.01) |
| C07C 29/145 | (2006.01) |
| C07C 37/08 | (2006.01) |
| C07C 45/00 | (2006.01) |

(52) U.S. Cl.
CPC ............... *B01J 29/90* (2013.01); *B01J 29/084* (2013.01); *B01J 29/40* (2013.01); *B01J 29/70* (2013.01); *B01J 29/703* (2013.01); *B01J 29/7034* (2013.01); *B01J 29/7038* (2013.01); *B01J 29/7042* (2013.01); *B01J 29/7046* (2013.01); *B01J 38/04* (2013.01); *B01J 38/10* (2013.01); *C07C 2/864* (2013.01); *C07C 29/145* (2013.01); *C07C 37/08* (2013.01); *C07C 45/00* (2013.01); *C07C 407/00* (2013.01); *C07C 2529/70* (2013.01)

(58) Field of Classification Search
USPC .......................................... 568/385, 616, 798
See application file for complete search history.

(56) References Cited

U.S. PATENT DOCUMENTS

| | | |
|---|---|---|
| 2003/0149314 A1 | 8/2003 | Chewter et al. |
| 2007/0142212 A1 * | 6/2007 | Pujado ............................ 502/34 |
| 2011/0201858 A1 * | 8/2011 | Hwang et al. ................. 585/314 |

FOREIGN PATENT DOCUMENTS

| | | | |
|---|---|---|---|
| EP | 1068898 A2 | 1/2001 | |

OTHER PUBLICATIONS

International Search Report and Written Opinion issued in the corresponding PCT/US2013/049079 on Nov. 8, 2013.
K. Joseph Antony Raj et al.: "Shape-selective reactions with AEL and AFI type molecular sieves alkylation of benzene, toluene and ethylbenzene with ethanol, 2-propanol, methanol and t-butanol", Journal of Molecular Catalysis A: Chemical 243 (2006) 99-105.
Binitha N. Narayanan et al.: "Selective Formation of Cumene on Pillared Clays by Isopropylation of Benzene", React.Kin et. Catal. Lett. vol. 89, No. 1, 45-53, (2006).

\* cited by examiner

*Primary Examiner* — Sudhakar Katakam
*Assistant Examiner* — Pancham Bakshi
(74) *Attorney, Agent, or Firm* — Robert Mlotkowski Safran & Cole, P.C.

(57) ABSTRACT

In a process for producing cumene, benzene and a C3 alkylating agent comprising isopropanol are supplied to an alkylation zone comprising a molecular sieve alkylation catalyst under alkylation conditions such that the isopropanol reacts with the benzene to produce a reaction product comprising cumene. Subsequently, the supply of benzene and C3 alkylating agent to the alkylation zone is ceased and a gaseous stripping agent is supplied to the molecular sieve alkylation catalyst under conditions effective to remove nitrogenous impurities deposited on the catalyst during the preceding alkylation reaction. The supply of benzene and C3 alkylating agent to the alkylation zone is then reinitiated.

17 Claims, No Drawings

PROCESS FOR PRODUCING CUMENE

CROSS-REFERENCE TO RELATED APPLICATIONS

The present application is a U.S. National Phase of PCT/US2013/051649 filed on Jul. 23, 2013 claiming priority to U.S. provisional application No. 61/675,942 filed Jul. 26, 2012. The disclosure of the PCT Application is hereby incorporated by reference into the present Application.

FIELD

This invention relates to a process for producing cumene and particularly, but not exclusively, to an integrated process for producing cumene and for converting the cumene to phenol.

BACKGROUND

Cumene is an important intermediate in the chemical and polymer industries, with global cumene production currently exceeding twelve million metric tons annually. The majority of all cumene manufactured in the world today is used for the production of phenol. The demand for phenol for the manufacture of Bisphenol-A and subsequently polycarbonates is accelerating, owing to the broadening applications of polycarbonates in the electronic, healthcare, and automobile industries.

The rapid growth of cumene, phenol and Bisphenol-A production, however, has caused some concerns related to the imbalance of the acetone byproduct produced from the phenol plant. Thus, acetone and phenol are produced at an approximately 1:1 molar ratio from cumene, but are used at an approximately 1:2 molar ratio in the downstream Bisphenol-A production process. The excess acetone that is not used in the production of Bisphenol-A has caused some concern from phenol producers in that it may create a supply-demand imbalance and disrupt the economics of the phenol production business.

In addition, cumene is typically produced by reacting benzene and propylene under liquid phase or mixed gas-liquid phase conditions in the presence of acid catalysts, particularly zeolite catalysts. The resultant need to locate integrated cumene/phenol plants near a source of propylene has become an important issue with producers. Thus, in today's olefins market, there is also a supply-demand imbalance in the supply of propylene produced from conventional sources, such as ethylene plants, due to the reduced availability of feedstocks that favor the production of propylene. This imbalance has forced phenol producers to build their plants closer to feedstock supplies rather than to product outlets.

Numerous research efforts have been directed at solving the acetone imbalance and propylene supply issues described above by employing the excess acetone produced in the phenol plant to produce cumene. For example, U.S. Pat. No. 5,015,786 teaches a process for preparing phenol, comprising the steps of: (a) alkylating benzene with isopropanol using a zeolite catalyst under liquid phase conditions to synthesize cumene, (b) oxidizing the cumene from step (a) with molecular oxygen into cumene hydroperoxide, (c) subjecting cumene hydroperoxide to acid cleavage to synthesize phenol and acetone, and (d) hydrogenating the acetone from step (c) with hydrogen gas under liquid phase conditions into isopropanol which is recycled to step (a).

One problem encountered in producing cumene from the excess acetone from a phenol plant is that the acetone tends to contain significant quantities of nitrogenous impurities which carry over into the isopropanol intermediate product. Such impurities act as poisons to the zeolite catalyst employed in the downstream alkylation step and so must be removed or reduced to very low levels. However, attempts to remove these impurities from the acetone and isopropanol feeds with conventional solid acid adsorbents have proved to be only marginally effective due to the molecular polarity of the acetone and isopropanol, which competes with the adsorption of the polar nitrogen compounds. Also, the high water solubility of acetone and isopropanol eliminates the use of water washing, which is also commonly employed to remove nitrogen compounds from hydrocarbon streams.

Despite these problems, various methods are being investigated for reducing the level of nitrogen impurities in the isopropanol feed to the zeolite alkylation catalyst. However, whatever method is employed, it is very difficult to reduce these levels to zero and so in practice the zeolite catalyst will have a limited cycle life owing to the build-up of nitrogen compounds at the active acid sites of the catalyst. There is therefore a need for a method of rejuvenating the spent catalyst from an isopropanol alkylation process so as to extend its cycle life.

U.S. Published Patent Application No. 2010/0285949 discloses a method for rejuvenating a catalyst, particularly a spent catalyst used in the alkylation of benzene with propylene to produce cumene. The catalyst comprises at least 10 wt. % of a molecular sieve selected from at least one of a MCM-22 family molecular sieve, a molecular sieve having a framework type of BEA, a molecular sieve having a framework type of FAU, and a molecular sieve having a framework type of MOR, wherein the spent catalyst also comprises from 0.001 wt. % to 45 wt. % of hydrocarbons and 0.001 to 10 wt. % nitrogen containing components. The rejuvenation method comprises contacting the spent catalyst with a gaseous feedstock comprising at least one of $N_2$, $H_2$, alkane, He, Ar, CO, and $CO_2$ for at least one hour at rejuvenation conditions comprising a temperature in the range from about 400 to 600° C., a pressure in the range from about 101.3 kPa-a to 10130 kPa-a, a space hourly velocity in the range of from 0.05 to 10 normal cubic meter gaseous feedstock per hour per kilogram of catalyst to form a rejuvenated catalyst and a gaseous product. The rejuvenated catalyst comprises at least 50 wt. % less nitrogen containing components than the catalyst prior to the contacting step, and the gaseous product comprises at least a portion of the gaseous feedstock and at least a portion of the hydrocarbons and the nitrogen containing components contained by the spent catalyst.

In accordance with the present invention, it has now been found that a spent zeolite catalyst deactivated in the alkylation of benzene with isopropanol can be successfully rejuvenated by treatment with a gaseous stripping agent, such as of $N_2$, $H_2$, alkane, He, Ar, CO, and $CO_2$. This is surprising since the spent catalyst contains nitrogenous contaminants, which originated in the phenol process and which are significantly different from the nitrogenous impurities deposited on the catalyst when used to produce cumene by alkylation of benzene with propylene, which are typically ammonia and amines. The nitrogenous impurities originating in the phenol process result from the use of steam condensate and caustic in washing steps in the phenol process Filming amines and nitrogenous corrosion inhibitors that are present in the steam condensate and caustic are transferred to cumene recycle streams in the phenol process. These components subsequently undergo chemical reaction in the oxidation and hydroperoxide cleavage steps of the phenol process creating highly polar and non-ideal components in the acetone product, such as imines and oximes. These impurities are substantially different in nature from the typical nitrogenous impurities present in the cumene process by alkylation of benzene and propylene.

SUMMARY

In one aspect, the invention resides in a process for producing cumene comprising:

(a) supplying benzene and a $C_3$ alkylating agent comprising isopropanol to an alkylation zone comprising a molecular sieve alkylation catalyst under alkylation conditions such that the isopropanol reacts with the benzene to produce a reaction product comprising cumene;

(b) ceasing the supply of benzene and $C_3$ alkylating agent to the alkylation zone;

(c) supplying a gaseous stripping agent to the molecular sieve alkylation catalyst under conditions to remove nitrogenous impurities deposited on the catalyst during (a); and (d) reinitiating the supply of benzene and $C_3$ alkylating agent to the alkylation zone.

Generally, the gaseous stripping agent comprises at least one of $N_2$, $H_2$, alkane, He, Ar, CO, and $CO_2$.

Typically, the conditions in (c) comprise a temperature in the range from about 100 to about 600° C. and a pressure in the range from about 120 kPa-a to about 2170 kPa-a.

In one embodiment, the supplying (c) is continued until the alkylation activity of the molecular sieve alkylation catalyst is increased to at least 60% of the alkylation activity of the fresh catalyst.

Conveniently, the supplying (c) is conducted with the molecular sieve alkylation catalyst being retained in the alkylation zone.

Generally, alkylation catalyst comprises at least one molecular sieve selected from the group comprising ZSM-3, ZSM-4, ZSM-5, ZSM-11, ZSM-12, ZSM-14, ZSM-18, ZSM-20, ZSM-22, ZSM-23, ZSM-35, ZSM-48, zeolite beta, zeolite Y, Ultrastable Y (USY), Dealuminized Y (Deal Y), mordenite, MCM-22, PSH-3, SSZ-25, ERB-1, ITQ-1, ITQ-2, MCM-36, MCM-49, MCM-56, and UZM-8.

In one embodiment, the $C_3$ alkylating agent also comprises propylene.

Generally, the process further comprises:

(e) oxidizing at least part of the cumene produced in (a) and (d) to form cumene hydroperoxide;

(f) cleaving at least part of the cumene hydroperoxide from (e) to form a cleavage effluent stream containing phenol and acetone;

(g) separating at least part of the acetone from the cleavage effluent stream;

(h) hydrogenating at least part of the acetone separated in (g) to produce isopropanol; and (f) recycling at least part of the isopropanol produced in (h) to (a) and/or (d).

DETAILED DESCRIPTION

A process is described for producing cumene by alkylation of benzene with a $C_3$ alkylating agent in the presence of an acidic alkylation catalyst, particularly a molecular sieve catalyst. The cumene is then converted by the Hock process to equimolar amounts of phenol and acetone which are in turn used at an approximately 2:1 molar ratio to produce Bisphenol-A. The resulting excess acetone is recovered and hydrogenated to produce isopropanol which is used as at least part of the $C_3$ alkylating agent in the present process. However, as will be discussed in more detail below, such isopropanol inherently contains nitrogenous impurities which act as poisons for the alkylation catalyst. Although various methods are being investigated for reducing the level of these impurities, in practice it is very difficult to reduce these levels to zero. Thus, the alkylation catalyst has a limited cycle live as nitrogen compounds build up at the active acid sites of the catalyst. The present process therefore provides an effective method of periodically rejuvenating the spent alkylation catalyst so as to extend its useful life.

Benzene Alkylation to Produce Cumene

In the first stage of the present process, benzene is alkylated with a $C_3$ alkylating agent comprising isopropanol, optionally together with added propylene, in the presence of a molecular sieve alkylation catalyst under conditions such that at least part of the reaction mixture is maintained in the liquid phase during the process. Typical conditions include a temperature of about 20° C. to about 350° C., for example about 60° C. to about 300° C., such as from 100 to 300° C., for example from 150 to 280° C., a pressure of about 100 kPa to about 20,000 kPa, for example about 500 kPa to about 10,000 kPa, and a molar ratio of benzene to the $C_3$ alkylating agent of about 0.1:1 to about 100:1, such as from 0.3:1 to 10:1, such as about 1:1 to about 10:1, for example from 0.5:1 to 5:1, such as from 1:1 to 3:1. Where the $C_3$ alkylating agent contains propylene, the molar ratio of isopropanol to propylene is typically about 1 to 100 to about 100 to 1.

Generally, the alkylation is conducted in the presence hydrogen, either added directly to the alkylation feed or present in the reactor effluent recycled from the fourth hydrogenation stage described below. Thus, it is found that hydrogen assists in removing the water coproduced with cumene in the alkylation step from the liquid phase reaction medium, thereby reducing the contact between the catalyst and the water and hence any tendency for the water to deactivate the catalyst. For some catalysts, the presence of hydrogen during the alkylation stage also reduces the deactivation caused by coke formation on the catalyst. Excessive hydrogen should, however, be avoided since it can lead to undesirable loss of benzene to cyclohexane. Conveniently, the molar ratio of hydrogen to isopropanol in said second reaction zone is about 0:1 to about 100:1, such as about 0:1 to about 10:1.

The catalyst employed in the alkylation step may comprise at least one medium pore molecular sieve having a Constraint Index of 2-12 (as defined in U.S. Pat. No. 4,016,218). Suitable medium pore molecular sieves include ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231.

Alternatively, the alkylation catalyst may comprise one or more large pore molecular sieves having a Constraint Index less than 2. Suitable large pore molecular sieves include zeolite beta, zeolite Y, Ultrastable Y (USY), Dealuminized Y (Deal Y), mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite Beta is described in U.S. Pat. No. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

Preferably, however, the alkylation catalyst comprises at least one molecular sieve of the MCM-22 family. As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Molecular sieves of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Pat. No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Related zeolite UZM-8 is also suitable for use as the present alkylation catalyst.

The above molecular sieves may be used as the alkylation catalyst without any binder or matrix, i.e., in so-called self-bound form. Alternatively, the molecular sieve may be composited with another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 percent by weight and more usually, particularly, when the composite is prepared in the form of beads, in the range of about 2 to about 80 weight percent of the composite.

The alkylation step may be carried out batchwise or on a continuous basis. Moreover, the reaction may be carried out in a fixed or moving bed reactor. Fixed bed operation is, however, preferred, typically with the alkylation reaction zone comprising one or a plurality of series-connected beds of alkylation catalysts.

As the alkylation reaction proceeds, the molecular sieve alkylation catalyst gradually loses activity as the acid sites are titrated by nitrogenous impurities in the isopropanol feed. At some convenient stage in the deactivation process, such as when the catalyst has lost 80% of its initial catalytic activity, the supply of $C_3$ alkylating agent and benzene to the catalyst is terminated and a gaseous stripping agent is supplied to the catalyst under conditions effective to remove at least some of the nitrogenous impurities deposited on the catalyst during the previous alkylation cycle. Suitable gaseous stripping agents include at least one of $N_2$, $H_2$, alkane, He, Ar, CO, and $CO_2$, while suitable stripping conditions include a temperature in the range from about 100 to about 600° C., such as from about 200 to about 500° C. and a pressure in the range from about 120 kPa-a to about 2170 kPa-a, such as about 200 kPa-a to about 1000 kPa-a. Normally the catalyst is retained in situ in the alkylation reactor during the stripping step, with the gaseous stripping agent being supplied to the catalyst countercurrent to the supply of benzene and $C_3$ alkylating agent during the previous alkylation cycle. Alternatively, the catalyst can be removed from the alkylation reactor and mounted in a separate stripping zone for the stripping operation.

The stripping step is generally conducted until the alkylation activity of the molecular sieve alkylation catalyst is increased to at least 60%, such as at least 75%, of the alkylation activity of the fresh catalyst. At that stage, the supply of stripping gas to the catalyst is terminated and the supply of benzene and $C_3$ alkylating agent to the alkylation zone is reinitiated and a new alkylation cycle is started. Alternating alkylation and rejuvenation cycles can then be repeated until rejuvenation is unable to return the catalyst to some minimum required alkylation activity.

Treatment of Alkylation Reactor Effluent

The alkylation step is generally operated so as to achieve substantially complete conversion of the $C_3$ alkylating agent (isopropanol plus any added propylene) and hence the effluent from the alkylation reactor is composed mainly of cumene, coproduced water, unreacted benzene, and other reaction products. Hydrogen will also be present in the effluent if it is present in the feed. Water and, if present, hydrogen, are initially removed from the effluent and an aliquot of the resultant dried effluent stream is then separated and recycled to the alkylation zone in order to control the reaction temperature and to control the water content in the alkylation reactor.

If hydrogen is present in the effluent, hydrogen removal is typically achieved by passing the effluent directly from the alkylation reactor into a vapor/liquid separator to divide the effluent into a hydrogen-rich vapor stream and a hydrogen-depleted liquid stream. The hydrogen-rich vapor stream can then be recycled to the alkylation reactor, generally after being compressed and cooled to separate any entrained water and aromatics. The hydrogen-depleted liquid stream is subsequently separated into a water-rich aqueous stream and a water-depleted aromatic stream comprising cumene, unreacted benzene, and other reaction products. If hydrogen is not present in the effluent, the effluent stream from the alkylation reactor can be cooled, separated into a water-rich aqueous stream and a water-depleted aromatic stream comprising cumene, unreacted benzene, and other reaction products.

After separation and recycle of an aliquot of the dried effluent stream, the remainder of the dried effluent stream is passed to a distillation column, where the cumene is recovered and a benzene recycle stream containing unreacted benzene is separated for recycle back to the alkylation reaction zone.

Cumene Oxidation

The cumene recovered from the alkylation reaction effluent is converted to cumene hydroperoxide by a liquid phase oxidation process which is preferably carried out in a plurality of reactors connected in series. The oxidation process is conducted in the presence of an oxygen-containing gas, generally air, at a temperature from 50 to 120° C. and a pressure of 0 to 1 MPaG (gauge pressure). The total residence time in the oxidation reactors is usually from 3 to 20 hours.

The oxidation reaction may be carried out with or without a catalyst. Where a catalyst is employed, suitable catalysts include basic materials, such as carbonate and hydroxide compounds of alkali metals, such as lithium, sodium and potassium, and alkaline earth metals such as calcium and magnesium. These compounds may be used in solid form or in aqueous solution. The amount of catalyst (metal basis) is usually not more than 10 g equivalent, preferably 0.1 to 6 g equivalent, per 1 ton of cumene.

The product of the oxidation reaction comprises a gas phase composed of spent air containing entrained cumene and a liquid phase which generally comprises 20 to 50% by weight of cumene hydroperoxide and 50 to 80% by weight of unreacted cumene, together with various by-products mainly composed of dimethyl phenyl carbinol (DMPC).

The gas phase product from the oxidation stage is cooled and then passed through a series of adsorbent beds, normally comprising charcoal, where the entrained cumene is removed before the spent air is vented to atmosphere or flared. The cumene collected by the charcoal adsorbers is recovered by desorption with low-pressure steam followed by condensation of the steam and decanting of the organic and water phases. The organic phase is then fed to a cumene recycle system described in more detail below.

The liquid phase product from the oxidation stage is heated in one or more stages, typically under vacuum, to remove most of the unreacted cumene and concentrate the cumene hydroperoxide in the product to 75 to 85 wt % before the product is fed to the cleavage step. The cumene vapor removed from the liquid phase product is cooled and combined with other cumene recycle streams produced in the process, such as the cumene recovered from the spent air, before being sent to the cumene recycle system.

Cumene Hydroperoxide Cleavage

The concentrated cumene hydroperoxide from the oxidation stage is decomposed or cleaved in the presence of an acid catalyst, normally sulfuric acid, mainly to phenol and acetone, while most of the DMPC by-product is converted to a-methylstyrene (AMS). The cleavage reaction is typically carried out at a temperature of about 40° C. to about 60° C. and a pressure of about 0 kPa to about 500 kPa.

The acid catalyst added to the cleavage reactor may be neutralized to prevent yield loss due to side reactions and to protect against corrosion in the downstream fractionation section. This is typically achieved by injecting caustic into the cleavage reactor effluent before the effluent passes to the fractionation section.

After neutralization, the cleavage effluent is initially passed to an acetone recovery section comprising at least a crude acetone recovery column and a finished acetone recovery column. In the crude acetone recovery column, the effluent is separated into a crude phenol bottoms stream, which is fed to a phenol recovery section, and a crude acetone overhead stream. The overhead stream is then fed to the finished acetone recovery column, where unreacted cumene and water are removed as a bottoms stream and acetone product is recovered as an overhead stream. After removal of the water, the unreacted cumene is sent to the cumene recycle system.

The crude phenol stream removed in the acetone recovery section is fed to a phenol recovery section which again comprises a multi-column distillation section, where a mixed cumene/AMS stream is removed before the crude phenol undergoes various chemical treatments and fractionation before a finished phenol product is recovered.

The mixed cumene/AMS stream removed in the phenol recovery section is initially subjected to a caustic wash to remove any residual acid and is then passed to a hydrogenation reactor where the AMS undergoes mild hydrogenation in the presence of a platinum catalyst to produce cumene with high selectivity. The resultant cumene enriched product is then sent to the cumene recycle system.

The cumene recycle system returns the unreacted and produced cumene generated in the process back to the cumene oxidation step. However, the cumene recycle streams contain acidic impurities generated and/or added during the oxidation and cleavage steps and their ancillary separation and purification units. In the cumene oxidation step these acidic impurities inhibit the oxidation reaction, and therefore the cumene recycle streams are treated with an aqueous caustic solution, such as sodium hydroxide solution, before being returned to the cumene oxidation stage. The caustic wash solution is produced by diluting concentrated caustic with demineralized water and condensed steam from the process. However, these process water streams tend to contain relatively high levels (up to 10 ppm by weight) of dissolved nitrogen compounds, particularly amines added to resist corrosion in the upstream distillation equipment. These nitrogen compounds are readily transferred to the organic phase at the high pH (normally from about 8 to about 14) used in the caustic washing step. Once transferred, these impurities tend to remain in the organic phase and pass from the cumene to the acetone produced by the cleavage reaction, typically after undergoing reaction in the oxidation and cleavage steps to products, such as imines and oximes.

Acetone Hydrogenation

Generally, the phenol and acetone recovered from the cleavage effluent are used in a molar ratio of 2:1 to produce Bisphenol A, thereby resulting in a net surplus of acetone. In the present process, the excess acetone from the cleavage stage is hydrogenated to produce isopropanol for recycle to alkylation stage. The acetone hydrogenation may be effected by contacting the excess acetone with hydrogen in the presence of metal-containing catalyst. Generally the catalyst is Raney nickel, but other useful catalysts include nickel, copper-chromium, Raney nickel-copper, copper-zinc and platinum group metals, for example, platinum, palladium, ruthenium, rhodium, and similar metals on active carbon, aluminum and other carriers. The reaction temperature may range from 20° C. to about 350° C., but more generally is between about 40° C. and 250° C., such as between about 60° C. and 200° C. The hydrogenation may be carried out by either liquid, gas, or mixed gas-liquid phase reaction. The pressure may range from 100 kPa to 20,000 kPa, such as from about 500 to about 10,000 kPa. The hydrogen gas is generally present in a molar ratio relative to the acetone reactant of from 0.1:1 to 100:1, such as from 1:1 to 10:1.

The hydrogenation may be carried out in the presence or absence of a reaction medium. Examples of suitable media include alcohols such as methanol, ethanol, propanols, and butanols. Also useful are glycols such as ethylene glycol, propylene glycol, diethylene glycol, and triethylene glycol; and ethers such as diisopropyl ether, dibutyl ether, ethylene glycol dimethyl ether, diglyme (diethylene glycol dimethyl ether) and triglyme. Aprotic polar solvents may also be used, for example, dimethylformamide, dimethylacetamide, acetonitrile, and dimethyl sulfoxide. Also useful are saturated hydrocarbons such as hexane, heptane, cyclopentane, and cyclohexane. Water can also be used as a solvent in the hydrogenation reaction.

The hydrogenation step may be carried out batchwise or on a continuous basis. Depending on the shape of a particular catalyst used, the reaction may be carried out in a fluidized bed using powder catalyst or a fixed bed using granular catalyst. Fixed bed operation is preferred in view of ease of separation of the catalyst from the reaction mixture and simplicity of the reaction system.

The hydrogenation reaction is exothermic and, to avoid excessive temperature rise, part of the reaction effluent, composed mainly of isopropanol, can be cooled and recycled to hydrogenation reactor inlet. In one embodiment, the weight ratio of liquid recycle to acetone feed is between about 1:1 and about 100:1.

In addition, part of the unreacted hydrogen in the hydrogenation reaction effluent can be recycled to the hydrogenation reactor inlet so as to reduce the level of hydrogen in the isopropanol-containing feed to the alkylation step.

The invention will now be more particularly described with reference to the following non-limiting Examples.

Example 1

Alkylation with Purchased Isopropanol

An alkylation test of benzene with isopropanol was carried out in a fixed bed reactor, made from a ¾ inch (19 mm) diameter Schedule 40 Stainless Steel 316 pipe with a total length of 34 inches (864 mm) A multi-point thermocouple probe was placed along the center axis of the reactor so that the temperature at various points in the reactor could be be monitored. A storage tank was used for the benzene/isopropanol mixture and a positive displacement pump was used for feeding the benzene/isopropanol mixture into the reactor. The flow rates of the benzene/isopropanol mixture were set by pump settings and monitored by electronic weight scales. The reactor operating conditions were controlled and monitored by an automatic control system. The reactor effluent was cooled to near ambient temperature and then the free water was removed in a decanter. A portion of the reactor effluent, after the free water was removed in the decanter, was circulated back to the reactor inlet by a centrifugal pump to control the temperature rise and the moisture content in the reactor.

The feedstock and reactor effluent were analyzed by two Hewlett Packard 5890 Series II Gas Chromatographs, one equipped with a Chrompack CP-Wax 52 CB column having an inside diameter of 0.25 mm, film thickness of 0.5 μm, and length of 60 meters, and the other one equipped with an Agilent DB-1 column having an inside diameter of 0.25 mm, film thickness of 0.5 μm, and length of 100 meters.

30 grams of an MCM-22 family catalyst was loaded into the fixed bed reactor and dried with benzene at 150° C. for four days. A feed comprised of 79.6 wt % benzene and 20.4 wt % isopropanol purchased from Sigma-Aldrich, equivalent to a benzene to isopropanol molar ratio of 3:1, was fed to the reactor at about 75 grams per hour, giving an isopropanol WHSV of 0.5 hr$^{-}$. No nitrogen compounds were detected in this purchased isopropanol. The reactor circulation was adjusted to give a moisture content of about 1.0 wt % in the reactor effluent. The inlet temperature was 210° C., the reactor pressure was maintained at about 4,700 kPa, and the reaction took place in liquid phase. The isopropanol conversion was 100% throughout the run. Because the isopropanol conversion was always at or very close to 100% throughout this example and Examples 3-6, the catalyst stability was also monitored by percent temperature rise at 26% catalyst loading ($PTR_{26}$) which is defined below:

$$PTR_{26}=[T_{26}-T_{inlet}]/[T_{outlet}-T_{inlet}]\times 100\%$$

where $T_{inlet}$ and $T_{outlet}$ are the reactor temperatures measured at the inlet and the outlet of the catalyst bed, respectively. $T_{26}$ is the temperature measured at 26% of the length from the inlet of the catalyst bed. Because the isopropanol alkylation is an exothermic reaction, the temperature of the reaction mixture goes up in the reactor as the conversion increases and reaches the final temperature when the reaction is completed. The percentage temperature rise $PTR_{26}$ measured at the first 26% of the catalyst loading gives an indication of the conversion in the first 26% of the catalyst bed. When the catalyst is stable, the conversion in the first 26% of the catalyst bed is stable and $PTR_{26}$ remains essentially constant. When the catalyst deactivates, the conversion in the first 26% of the catalyst bed goes down gradually (while the remainder of the catalyst bed continues to bring the reaction to completion) and the $PTR_{26}$ goes down. A stable $PTR_{26}$ therefore indicates that the catalyst bed is stable while a decreasing $PTR_{26}$ indicates that the catalyst bed is deactivating.

For 54 days, from 5 to 59 days on-stream with isopropanol feed purchased from Sigma-Aldrich, the $PTR_{26}$ remained at 100%. The isopropanol conversion remained at 100%. This indicates that the MCM-22 family catalyst tested had very high activity and was very stable with the purchased isopropanol feed.

Example 2

Hydrogenation of Acetone to Isopropanol

A batch of acetone obtained from a commercial phenol/acetone plant was hydrogenated to isopropanol by contacting the acetone feed with hydrogen in the presence of a nickel hydrogenation catalyst at a temperature of about 80° C. and a pressure of about 3,600 kPa. A portion of the reactor effluent was recycled back to the reactor inlet to keep the temperature rise below about 30° C. The acetone conversion was about 99%. The isopropanol product was found to contain about 0.2 wtppm nitrogen compounds.

Example 3

Alkylation with Isopropanol Produced from Acetone

The same reactor setup and catalyst loading described in Example 1 were used in this example. The $PTR_{26}$ was stable with feed comprised of 79.6 wt % benzene and 20.4 wt % isopropanol purchased from Sigma-Aldrich. All other operating conditions were the same as those in Example 1. At 102 days on-stream, feed comprised of 79.6 wt % benzene and 20.4 wt % of the isopropanol produced in Example 2 was introduced into the reactor, in place of the purchased acetone, while all the other operating conditions were kept the same as those in Example 1. A rapid and continuous decline of $PTR_{26}$ was detected immediately, indicating that the catalyst was being deactivated by the nitrogen compounds in the produced isopropanol.

Example 4

Gas Stripping with Nitrogen

The same reactor setup and catalyst loading described in Example 3 were used in this example. At 112 days on-stream, the $PTR_{26}$ and isopropanol conversion was 73% and 99.9983%, respectively. The benzene/isopropanol feed to the reactor was stopped and the reactor was cooled down to ambient temperature under a benzene purge. The benzene purged was stopped and the reactor pressure lowered to atmospheric pressure. After the liquid in the reactor was drained, a nitrogen purge stream was introduced into the reactor at about 700 kPa countercurrent to the benzene/isopropanol feed and the reactor was heated up at about 1° C. per minute to about 478° C. and held between 478 and 488° C. for 36 hours.

The reactor temperature was then lowered to ambient temperature at about 1° C. per hour and then the nitrogen purge terminated. Benzene feed was introduced into the reactor and the reactor pressure raised to 4,700 kPa. The reactor temperature was raised to 210° C. and a feed comprised of 79.6 wt % benzene and 20.4 wt % isopropanol purchased from Sigma-Aldrich introduced into the reactor. All the other operating conditions were kept the same as those in Example 1. After the catalyst was lined-out with the benzene/isopropanol feed, the $PTR_{26}$ was found to be 95%, indicating that the catalyst activity has been significantly recovered. The isopropanol conversion was 99.9996%, indicating that about 76% of the lost isopropanol conversion was recovered.

Example 5

Alkylation with Isopropanol Produced from Acetone

The same reactor setup and catalyst loading described in Example 4 were used in this example. At 129 days on-stream, feed comprised of 79.6 wt % benzene and 20.4 wt % of the isopropanol produced in Example 2 was introduced into the reactor, in place of the purchased acetone, while all the other operating conditions were kept the same as those in Example 1. A rapid and continuous decline of $PTR_{26}$ started immediately, indicating that the catalyst was being deactivated by the nitrogen compounds in the produced isopropanol.

Example 6

Gas Stripping with Hydrogen

The same reactor setup and catalyst loading described in Example 5 were used in this example. At 142 days on-stream, the $PTR_{26}$ was 67% with the isopropanol produced in Example 2. The isopropanol conversion was 99.9960%. The benzene/isopropanol feed to the reactor was stopped and the reactor cooled down to ambient temperature under a benzene purge. The benzene purged was stopped and the reactor pressure lowered to atmospheric pressure. After the liquid in the reactor was drained, a hydrogen purge stream was introduced into the reactor at about 700 kPa countercurrent to the benzene/isopropanol feed. The reactor was then heated up at about 1° C. per minute to about 385° C. and held between 383 and 385° C. for 48 hours.

The reactor temperature was then lowered to ambient temperature at about 1° C. per hour and then the hydrogen purge terminated. Benzene feed was introduced into the reactor and the reactor pressure raised to 4,700 kPa. The reactor temperature was raised to 210° C. and then a feed comprised of 79.6 wt % benzene and 20.4 wt % isopropanol purchased from Sigma-Aldrich introduced into the reactor. All the other operating conditions were kept the same as those in Example 1. After the catalyst was lined-out with the benzene/isopropanol feed, the $PTR_{26}$ was found to be 91%, indicating that the catalyst activity had been significantly recovered. The isopropanol conversion was 99.9989%, indicating that about 73% of the lost isopropanol conversion was recovered.

The $PTR_{26}$ and isopropanol conversion observed in Examples 1, 4 and 6 are listed in Table 1.

TABLE 1

Effect of Gas Stripping

| | $PTR_{26}$ | Isopropanol Conversion |
|---|---|---|
| Fresh catalyst (Example 1) | 100% | 100% |
| Before Nitrogen Stripping (Example 4) | 73% | 99.9983% |
| After Nitrogen Stripping (Example 4) | 95% | 99.9996% |
| Before Hydrogen Stripping (Example 6) | 67% | 99.9960% |
| After Hydrogen Stripping (Example 6) | 91% | 99.9989% |

It is clear from Table 1 that the activity of catalyst was significantly recovered by each of the two gas stripping tests carried out in Examples 4 and 6. These Examples also demonstrate that the activity of the catalyst deactivated by nitrogenous species contained in isopropanol can be significantly recovered while the catalyst was retained in the reactor. The run length of the isopropanol alkylation catalyst can therefore be significantly enhanced by gas stripping without removing the catalyst from the alkylation zone.

The invention claimed is:
1. A process for producing cumene comprising:
   (a) supplying benzene and a $C_3$ alkylating agent comprising isopropanol to an alkylation zone comprising a molecular sieve alkylation catalyst under alkylation conditions such that the isopropanol reacts with the benzene to produce a reaction product comprising cumene;
   (b) ceasing the supply of benzene and $C_3$ alkylating agent to the alkylation zone;
   (c) supplying a gaseous stripping agent to the molecular sieve alkylation catalyst under conditions to remove nitrogenous impurities deposited on the catalyst during (a); and
   (d) reinitiating the supply of benzene and $C_3$ alkylating agent to the alkylation zone to produce the reaction product comprising cumene.
2. The process of claim 1, wherein said gaseous stripping agent comprises at least one of $N_2$, $H_2$, alkane, He, Ar, CO, and $CO_2$.

3. The process of claim 1, wherein said conditions in (c) comprise a temperature in the range from about 100 to about 600° C. and a pressure in the range from about 120 kPa-a to about 2170 kPa-a.

4. The process of claim 1, wherein the supplying (c) is continued until the alkylation activity of the molecular sieve alkylation catalyst is increased to at least 60% of the alkylation activity of the fresh catalyst.

5. The process of claim 1, wherein said supplying (c) is conducted with the molecular sieve alkylation catalyst being retained in the alkylation zone.

6. The process of claim 5, wherein said gaseous stripping agent is supplied to the molecular sieve alkylation catalyst in (c) countercurrent to the supply of benzene and $C_3$ alkylating agent in (a).

7. The process of claim 1, wherein hydrogen is also supplied to the alkylation zone in (a).

8. The process of claim 1, wherein said alkylation catalyst comprises at least one molecular sieve selected from the group comprising ZSM-3, ZSM-4, ZSM-5, ZSM-11, ZSM-12, ZSM-14, ZSM-18, ZSM-20, ZSM-22, ZSM-23, ZSM-35, ZSM-48, zeolite beta, zeolite Y, Ultrastable Y (USY), Dealuminized Y (Deal Y), mordenite, MCM-22, PSH-3, SSZ-25, ERB-1, ITQ-1, ITQ-2, MCM-36, MCM-49, MCM-56, and UZM-8.

9. The process of claim 1, wherein said alkylation catalyst comprises at least one molecular sieve selected from the group comprising MCM-22, PSH-3, SSZ-25, ERB-1, ITQ-1, ITQ-2, MCM-36, MCM-49, MCM-56 and UZM-8.

10. The process of claim 1, wherein said alkylation conditions comprise a temperature of 20° C. to 350° C., a pressure of 100 kPa to 20,000 kPa, and a molar ratio of benzene to $C_3$ alkylating agent fed to said alkylation zone of 0.1:1 to 100:1.

11. The process of claim 10, wherein the molar ratio of benzene to $C_3$ alkylating agent fed to said alkylation zone ranges from 0.3:1 to 10:1.

12. The process of claim 10, wherein the temperature in (a) ranges from 100 to 300° C.

13. The process of claim 1, wherein said $C_3$ alkylating agent comprises a mixture of isopropanol and propylene at molar ratio of isopropanol to propylene of about 0.01:1 to about 100:1.

14. The process of claim 1 and further comprising:
(e) oxidizing at least part of the cumene produced in (a) and (d) to form cumene hydroperoxide;
(f) cleaving at least part of the cumene hydroperoxide from (e) to form a cleavage effluent stream containing phenol and acetone;
(g) separating at least part of the acetone from the cleavage effluent stream;
(h) hydrogenating at least part of the acetone separated in (g) to produce isopropanol; and
(f) recycling at least part of the isopropanol produced in (h) to (a) and/or (d).

15. The process of claim 10, wherein the molar ratio of benzene to $C_3$ alkylating agent fed to said alkylation zone ranges from 0.5:1 to 5:1.

16. The process of claim 10, wherein the molar ratio of benzene to $C_3$ alkylating agent fed to said alkylation zone ranges from 1:1 to 3:1.

17. The process of claim 10, wherein the temperature in (a) ranges from 150 to 280° C.

* * * * *